US010329616B2

(12) United States Patent
Lee et al.

(10) Patent No.: US 10,329,616 B2
(45) Date of Patent: Jun. 25, 2019

(54) PRIMER SET FOR PREPARATION OF NGS LIBRARY AND METHOD AND KIT FOR MAKING NGS LIBRARY USING THE SAME

(71) Applicant: Republic of Korea (Nat'l Forensic Service Dir., Ministry of Public Admin. and Security), Gangwon-do (KR)

(72) Inventors: Yang-Han Lee, Gangwon-do (KR); Chong Min Chung, Gangwon-do (KR); Min-Hee Kim, Gangwon-do (KR); Eu-Ree An, Gangwon-do (KR); Min Young Lee, Gangwon-do (KR)

(73) Assignee: REPUBLIC OF KOREA (NATIONAL FORENSIC SERVICE DIRECTOR, MINISTRY OF PUBLIC ADMINISTRATION & SECURITY), Gangwon-Do (KR)

( * ) Notice: Subject to any disclaimer, the term of this patent is extended or adjusted under 35 U.S.C. 154(b) by 282 days.

(21) Appl. No.: 15/334,998

(22) Filed: Oct. 26, 2016

(65) Prior Publication Data
US 2017/0121765 A1    May 4, 2017

(30) Foreign Application Priority Data

Oct. 28, 2015   (KR) ........................ 10-2015-0150278

(51) Int. Cl.
*C12Q 1/68*       (2018.01)
*C12Q 1/6874*     (2018.01)
*C12Q 1/6806*     (2018.01)

(52) U.S. Cl.
CPC ......... *C12Q 1/6874* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 4,437,975 | A | 3/1984 | Gillespie et al. |
| 4,683,195 | A | 7/1987 | Mullis et al. |
| 4,683,202 | A | 7/1987 | Mullis |
| 4,800,159 | A | 1/1989 | Mullis et al. |
| 4,988,617 | A | 1/1991 | Landegren et al. |
| 5,130,238 | A | 7/1992 | Malek et al. |
| 5,242,794 | A | 9/1993 | Whiteley et al. |
| 5,409,818 | A | 4/1995 | Davey et al. |
| 5,413,909 | A | 5/1995 | Bassam et al. |
| 5,494,810 | A | 2/1996 | Barany et al. |
| 5,554,517 | A | 9/1996 | Davey et al. |
| 5,861,245 | A | 1/1999 | McClelland et al. |
| 6,063,603 | A | 5/2000 | Davey et al. |
| 6,410,276 | B1 | 6/2002 | Burg et al. |
| 6,582,938 | B1 | 6/2003 | Su et al. |
| 7,432,049 | B2 * | 10/2008 | Liew ............... C12Q 1/6883 435/6.18 |
| 2013/0237432 | A1 | 9/2013 | Li et al. |
| 2014/0148364 | A1 | 5/2014 | Miled |

FOREIGN PATENT DOCUMENTS

| | | | | |
|---|---|---|---|---|
| EP | | 0329822 B1 | 6/1994 | |
| EP | | 0439182 B1 | 4/1996 | |
| JP | | 2009502137 A | 1/2009 | |
| JP | | 2013529471 A | 7/2013 | |
| JP | | 2015180193 A | 10/2015 | |
| KR | | 10-0746872 B1 | 8/2007 | |
| WO | | 8810315 A1 | 12/1988 | |
| WO | | 8906700 A1 | 7/1989 | |
| WO | | 9001069 A1 | 2/1990 | |
| WO | | 9006995 A1 | 6/1990 | |
| WO | | WO-03093506 A2 * | 11/2003 | ........... C12Q 1/6883 |
| WO | | WO-2012040387 A1 * | 3/2012 | ........... C12Q 1/6837 |
| WO | | WO2013096802 A1 | 6/2013 | |
| WO | | WO2014210353 A2 | 12/2014 | |
| WO | | WO2015056103 A2 | 4/2015 | |
| WO | | WO2015089462 A1 | 6/2015 | |
| WO | | WO2015108663 A1 | 7/2015 | |

OTHER PUBLICATIONS

Maricic et al. (PLoS one, 2010, 5(11):e14004, p. 1-5) (Year: 2010).*
Matsui et al. (2014, Biomed Res Int, vol. 2014, 303451, p. 1-10) (Year: 2014).*
Lowe et al. (Nucleic Acids Research, 1990, 18(7):1757-1761) (Year: 1990).*
McPherson, M.J., et al., "PCR", "Springer-Verlag New York Inc.", 2000, Publisher: BIOS Scientific Publishers.
NOTE: For the non-patent literature citations that no month of publication is indicated, the year of publication is more than 1 year prior to the effective filing date of the present application.
Edited by Sambrook, J., et al., "Amplification of cDNA Generated by Reverse Transcription of mRNA", "Molecular Cloning: A Laboratory Manual, 3rd ed.", 2001, pp. 8.46-8.53, Publisher: Cold Spring Harbor Press.
Kircher, M., et al., "Double Indexing Overcomes Inaccuracies in Multiplex Sequencing on the Illumina Platform", "Nucleic Acids Research", 2012, p. 1-8, vol. 40, No. 1.

* cited by examiner

*Primary Examiner* — Stephanie K Mummert
(74) *Attorney, Agent, or Firm* — Hultquist, PLLC; Steven J. Hultquist

(57) ABSTRACT

The present disclosure relates to a primer set for preparation of a library used for next generation sequencing (NGS), and a method and a kit for making an NGS library using the same. The method for making the next generation sequencing (NGS) library using the primer set according to the present disclosure is able to simply analyze large amounts of samples as compared to the existing method for making a library, which is effectively usable for analysis of target DNA sequences or for database construction, in large amounts of samples.

15 Claims, 2 Drawing Sheets
Specification includes a Sequence Listing.

FIG. 3

| | 1 | 2 | 3 | 4 | 5 | 6 | 7 | 8 | 9 | 10 | 11 | 12 |
|---|---|---|---|---|---|---|---|---|---|---|---|---|
| A | P1-R1 | P1-R2 | P1-R3 | P1-R4 | P1-R5 | P1-R6 | P1-R7 | P1-R8 | P1-R9 | P1-R10 | P1-R11 | P1-R12 |
| B | P2-R1 | P2-R2 | P2-R3 | P2-R4 | P2-R5 | P2-R6 | P2-R7 | P2-R8 | P2-R9 | P2-R10 | P2-R11 | P2-R12 |
| C | P3-R1 | P3-R2 | P3-R3 | P3-R4 | P3-R5 | P3-R6 | P3-R7 | P3-R8 | P3-R9 | P3-R10 | P3-R11 | P3-R12 |
| D | P4-R1 | P4-R2 | P4-R3 | P4-R4 | P4-R5 | P4-R6 | P4-R7 | P4-R8 | P4-R9 | P4-R10 | P4-R11 | P4-R12 |
| E | P5-R1 | P5-R2 | P5-R3 | P5-R4 | P5-R5 | P5-R6 | P5-R7 | P5-R8 | P5-R9 | P5-R10 | P5-R11 | P5-R12 |
| F | P6-R1 | P6-R2 | P6-R3 | P6-R4 | P6-R5 | P6-R6 | P6-R7 | P6-R8 | P6-R9 | P6-R10 | P6-R11 | P6-R12 |
| G | P7-R1 | P7-R2 | P7-R3 | P7-R4 | P7-R5 | P7-R6 | P7-R7 | P7-R8 | P7-R9 | P7-R10 | P7-R11 | P7-R12 |
| H | P8-R1 | P8-R2 | P8-R3 | P8-R4 | P8-R5 | P8-R6 | P8-R7 | P8-R8 | P8-R9 | P8-R10 | P8-R11 | P8-R12 |

FIG. 4

| | | # of base call | Total alignment base | % |
|---|---|---|---|---|
| HV1 | Match | 30666 | 30690 | 99.92 |
| | Mismatch | 24 | 30690 | 0.078 |
| | No call | 15 | 30690 | 0.049 |
| | Difference call | 3 | 30690 | 0.01 |
| | Heteroplasmy call | 6 | 30690 | 0.02 |

| | | # of base call | Total alignment base | % |
|---|---|---|---|---|
| HV2 | Match | 17275 | 17280 | 99.97 |
| | Mismatch | 5 | 17280 | 0.028 |
| | No call | | 17280 | 0 |
| | Difference call | | 17280 | 0 |
| | Heteroplasmy call | 6 | 17280 | 0.028 |

SEQUENCE LISTING

<160> NUMBER OF SEQ ID NOS: 68

<210> SEQ ID NO 1
<211> LENGTH: 29
<212> TYPE: DNA
<213> ORGANISM: Artificial Sequence
<220> FEATURE:
<223> OTHER INFORMATION: P5

<400> SEQUENCE: 1
aatgatacgg cgaccaccga gatctacac                                    29

<210> SEQ ID NO 2
<211> LENGTH: 24
<212> TYPE: DNA
<213> ORGANISM: Artificial Sequence
<220> FEATURE:
<223> OTHER INFORMATION: P7

<400> SEQUENCE: 2
caagcagaag acggcatacg agat                                         24

<210> SEQ ID NO 3
<211> LENGTH: 8
<212> TYPE: DNA
<213> ORGANISM: Artificial Sequence
<220> FEATURE:
<223> OTHER INFORMATION: D501

<400> SEQUENCE: 3 tatagcct                                                            8

<210> SEQ ID NO 4
<211> LENGTH: 8
<212> TYPE: DNA
<213> ORGANISM: Artificial Sequence
<220> FEATURE:
<223> OTHER INFORMATION: D502

<400> SEQUENCE: 4 atagaggc                                                            8

<210> SEQ ID NO 5
<211> LENGTH: 8
<212> TYPE: DNA
<213> ORGANISM: Artificial Sequence
<220> FEATURE:
<223> OTHER INFORMATION: D503

<400> SEQUENCE: 5 cctatcct                                                            8

<210> SEQ ID NO 6
<211> LENGTH: 8
<212> TYPE: DNA
<213> ORGANISM: Artificial Sequence
<220> FEATURE:
<223> OTHER INFORMATION: D504

<400> SEQUENCE: 6 ggctctga                                                            8

<210> SEQ ID NO 7
<211> LENGTH: 8
<212> TYPE: DNA
<213> ORGANISM: Artificial Sequence

```
<220> FEATURE:
<223> OTHER INFORMATION: D505

<400> SEQUENCE: 7 aggcgaag                                                                 8

<210> SEQ ID NO 8
<211> LENGTH: 8
<212> TYPE: DNA
<213> ORGANISM: Artificial Sequence
<220> FEATURE:
<223> OTHER INFORMATION: D506

<400> SEQUENCE: 8 taatctta                                                                 8

<210> SEQ ID NO 9
<211> LENGTH: 8
<212> TYPE: DNA
<213> ORGANISM: Artificial Sequence
<220> FEATURE:
<223> OTHER INFORMATION: D507

<400> SEQUENCE: 9 caggacgt                                                                 8

<210> SEQ ID NO 10
<211> LENGTH: 8
<212> TYPE: DNA
<213> ORGANISM: Artificial Sequence
<220> FEATURE:
<223> OTHER INFORMATION: D508

<400> SEQUENCE: 10 gtactgac                                                                 8

<210> SEQ ID NO 11
<211> LENGTH: 8
<212> TYPE: DNA
<213> ORGANISM: Artificial Sequence
<220> FEATURE:
<223> OTHER INFORMATION: D701

<400> SEQUENCE: 11 cgagtaat                                                                 8

<210> SEQ ID NO 12
<211> LENGTH: 8
<212> TYPE: DNA
<213> ORGANISM: Artificial Sequence
<220> FEATURE:
<223> OTHER INFORMATION: D702

<400> SEQUENCE: 12 tctccgga                                                                 8

<210> SEQ ID NO 13
<211> LENGTH: 8
<212> TYPE: DNA
<213> ORGANISM: Artificial Sequence
<220> FEATURE:
<223> OTHER INFORMATION: D703

<400> SEQUENCE: 13 aatgagcg                                                                 8
```

```
<210> SEQ ID NO 14
<211> LENGTH: 8
<212> TYPE: DNA
<213> ORGANISM: Artificial Sequence
<220> FEATURE:
<223> OTHER INFORMATION: D704

<400> SEQUENCE: 14 ggaatctc                                                                   8

<210> SEQ ID NO 15
<211> LENGTH: 8
<212> TYPE: DNA
<213> ORGANISM: Artificial Sequence
<220> FEATURE:
<223> OTHER INFORMATION: D705

<400> SEQUENCE: 15 ttctgaat                                                                   8

<210> SEQ ID NO 16
<211> LENGTH: 8
<212> TYPE: DNA
<213> ORGANISM: Artificial Sequence
<220> FEATURE:
<223> OTHER INFORMATION: D706

<400> SEQUENCE: 16 acgaattc                                                                   8

<210> SEQ ID NO 17
<211> LENGTH: 8
<212> TYPE: DNA
<213> ORGANISM: Artificial Sequence
<220> FEATURE:
<223> OTHER INFORMATION: D707

<400> SEQUENCE: 17 agcttcag                                                                   8

<210> SEQ ID NO 18
<211> LENGTH: 8
<212> TYPE: DNA
<213> ORGANISM: Artificial Sequence
<220> FEATURE:
<223> OTHER INFORMATION: D708

<400> SEQUENCE: 18 gcgcatta                                                                   8

<210> SEQ ID NO 19
<211> LENGTH: 8
<212> TYPE: DNA
<213> ORGANISM: Artificial Sequence
<220> FEATURE:
<223> OTHER INFORMATION: D709

<400> SEQUENCE: 19 catagccg                                                                   8

<210> SEQ ID NO 20
<211> LENGTH: 8
<212> TYPE: DNA
<213> ORGANISM: Artificial Sequence
<220> FEATURE:
<223> OTHER INFORMATION: D7010
```

```
<400> SEQUENCE: 20 ttcgcgga                                                                8

<210> SEQ ID NO 21
<211> LENGTH: 8
<212> TYPE: DNA
<213> ORGANISM: Artificial Sequence
<220> FEATURE:
<223> OTHER INFORMATION: D7011

<400> SEQUENCE: 21 gcgcgaga                                                                8

<210> SEQ ID NO 22
<211> LENGTH: 8
<212> TYPE: DNA
<213> ORGANISM: Artificial Sequence
<220> FEATURE:
<223> OTHER INFORMATION: D7012

<400> SEQUENCE: 22 gcgcgaga                                                                8

<210> SEQ ID NO 23
<211> LENGTH: 33
<212> TYPE: DNA
<213> ORGANISM: Artificial Sequence
<220> FEATURE:
<223> OTHER INFORMATION: Sequencing primer 1

<400> SEQUENCE: 23
acactctttc cctacacgac gctcttccga tct                                   33

<210> SEQ ID NO 24
<211> LENGTH: 34
<212> TYPE: DNA
<213> ORGANISM: Artificial Sequence
<220> FEATURE:
<223> OTHER INFORMATION: Sequencing primer 2

<400> SEQUENCE: 24
gtgactggag ttcagacgtg tgctcttccg atct                                  34

<210> SEQ ID NO 25
<211> LENGTH: 20
<212> TYPE: DNA
<213> ORGANISM: Artificial Sequence
<220> FEATURE:
<223> OTHER INFORMATION: HV 1-1

<400> SEQUENCE: 25
ctccaccatt agcacccaaa                                                  20

<210> SEQ ID NO 26
<211> LENGTH: 18
<212> TYPE: DNA
<213> ORGANISM: Artificial Sequence
<220> FEATURE:
<223> OTHER INFORMATION: HV 1-2

<400> SEQUENCE: 26
gaggatggtg gtcaaggg                                                    18

<210> SEQ ID NO 27
```

```
<210> SEQ ID NO 27
<211> LENGTH: 90
<212> TYPE: DNA
<213> ORGANISM: Artificial Sequence
<220> FEATURE:
<223> OTHER INFORMATION: HV 1-F1

<400> SEQUENCE: 27
aatgatacgg cgaccaccga gatctacacc ctatcctaca ctctttccct acacgacgct      60
cttccgatct ctccaccatt agcacccaaa                                      90

<210> SEQ ID NO 28
<211> LENGTH: 90
<212> TYPE: DNA
<213> ORGANISM: Artificial Sequence
<220> FEATURE:
<223> OTHER INFORMATION: HV 1-F2

<400> SEQUENCE: 28
aatgatacgg cgaccaccga gatctacacg gctctgaaca ctctttccct acacgacgct      60
cttccgatct ctccaccatt agcacccaaa                                      90

<210> SEQ ID NO 29
<211> LENGTH: 90
<212> TYPE: DNA
<213> ORGANISM: Artificial Sequence
<220> FEATURE:
<223> OTHER INFORMATION: HV 1-F3

<400> SEQUENCE: 29
aatgatacgg cgaccaccga gatctacact atagcctaca ctctttccct acacgacgct      60
cttccgatct ctccaccatt agcacccaaa                                      90

<210> SEQ ID NO 30
<211> LENGTH: 90
<212> TYPE: DNA
<213> ORGANISM: Artificial Sequence
<220> FEATURE:
<223> OTHER INFORMATION: HV 1-F4

<400> SEQUENCE: 30
aatgatacgg cgaccaccga gatctacaca tagaggcaca ctctttccct acacgacgct      60
cttccgatct ctccaccatt agcacccaaa                                      90

<210> SEQ ID NO 31
<211> LENGTH: 90
<212> TYPE: DNA
<213> ORGANISM: Artificial Sequence
<220> FEATURE:
<223> OTHER INFORMATION: HV 1-F5

<400> SEQUENCE: 31
aatgatacgg cgaccaccga gatctacaca ggcgaagaca ctctttccct acacgacgct      60
cttccgatct ctccaccatt agcacccaaa                                      90

<210> SEQ ID NO 32
<211> LENGTH: 90
<212> TYPE: DNA
<213> ORGANISM: Artificial Sequence
<220> FEATURE:
<223> OTHER INFORMATION: HV 1-F6

<400> SEQUENCE: 32
aatgatacgg cgaccaccga gatctacact aatcttaaca ctctttccct acacgacgct      60
```
cttccgatct ctccaccatt agcacccaaa                                         90

<210> SEQ ID NO 33
<211> LENGTH: 90
<212> TYPE: DNA
<213> ORGANISM: Artificial Sequence
<220> FEATURE:
<223> OTHER INFORMATION: HV 1-F7

<400> SEQUENCE: 33
aatgatacgg cgaccaccga gatctacacc aggacgtaca ctctttccct acacgacgct         60
cttccgatct ctccaccatt agcacccaaa                                         90

<210> SEQ ID NO 34
<211> LENGTH: 90
<212> TYPE: DNA
<213> ORGANISM: Artificial Sequence
<220> FEATURE:
<223> OTHER INFORMATION: HV 1-F8

<400> SEQUENCE: 34
aatgatacgg cgaccaccga gatctacacg tactgacaca ctctttccct acacgacgct         60
cttccgatct ctccaccatt agcacccaaa                                         90

<210> SEQ ID NO 35
<211> LENGTH: 84
<212> TYPE: DNA
<213> ORGANISM: Artificial Sequence
<220> FEATURE:
<223> OTHER INFORMATION: HV 1-R1

<400> SEQUENCE: 35
caagcagaag acggcatacg agatcgagta atgtgactgg agttcagacg tgtgctcttc         60
cgatctgagg atggtggtca aggg                                               84

<210> SEQ ID NO 36
<211> LENGTH: 84
<212> TYPE: DNA
<213> ORGANISM: Artificial Sequence
<220> FEATURE:
<223> OTHER INFORMATION: HV 1-R2

<400> SEQUENCE: 36
caagcagaag acggcatacg agattctccg gagtgactgg agttcagacg tgtgctcttc         60
cgatctgagg atggtggtca aggg                                               84

<210> SEQ ID NO 37
<211> LENGTH: 84
<212> TYPE: DNA
<213> ORGANISM: Artificial Sequence
<220> FEATURE:
<223> OTHER INFORMATION: HV 1-R3

<400> SEQUENCE: 37
caagcagaag acggcatacg agataatgag cggtgactgg agttcagacg tgtgctcttc         60
cgatctgagg atggtggtca aggg                                               84

<210> SEQ ID NO 38
<211> LENGTH: 84
<212> TYPE: DNA
<213> ORGANISM: Artificial Sequence
<220> FEATURE:

<223> OTHER INFORMATION: HV 1-R4

<400> SEQUENCE: 38
caagcagaag acggcatacg agatggaatc tcgtgactgg agttcagacg tgtgctcttc    60
cgatctgagg atggtggtca aggg    84

<210> SEQ ID NO 39
<211> LENGTH: 84
<212> TYPE: DNA
<213> ORGANISM: Artificial Sequence
<220> FEATURE:
<223> OTHER INFORMATION: HV 1-R5

<400> SEQUENCE: 39
caagcagaag acggcatacg agatttctga atgtgactgg agttcagacg tgtgctcttc    60
cgatctgagg atggtggtca aggg    84

<210> SEQ ID NO 40
<211> LENGTH: 84
<212> TYPE: DNA
<213> ORGANISM: Artificial Sequence
<220> FEATURE:
<223> OTHER INFORMATION: HV 1-R6

<400> SEQUENCE: 40
caagcagaag acggcatacg agatacgaat tcgtgactgg agttcagacg tgtgctcttc    60
cgatctgagg atggtggtca aggg    84

<210> SEQ ID NO 41
<211> LENGTH: 84
<212> TYPE: DNA
<213> ORGANISM: Artificial Sequence
<220> FEATURE:
<223> OTHER INFORMATION: HV 1-R7

<400> SEQUENCE: 41
caagcagaag acggcatacg agatagcttc aggtgactgg agttcagacg tgtgctcttc    60
cgatctgagg atggtggtca aggg    84

<210> SEQ ID NO 42
<211> LENGTH: 84
<212> TYPE: DNA
<213> ORGANISM: Artificial Sequence
<220> FEATURE:
<223> OTHER INFORMATION: HV 1-R8

<400> SEQUENCE: 42
caagcagaag acggcatacg agatgcgcat tagtgactgg agttcagacg tgtgctcttc    60
cgatctgagg atggtggtca aggg    84

<210> SEQ ID NO 43
<211> LENGTH: 84
<212> TYPE: DNA
<213> ORGANISM: Artificial Sequence
<220> FEATURE:
<223> OTHER INFORMATION: HV 1-R9

<400> SEQUENCE: 43
caagcagaag acggcatacg agatcatagc cggtgactgg agttcagacg tgtgctcttc    60
cgatctgagg atggtggtca aggg    84

<210> SEQ ID NO 44
<211> LENGTH: 84
<212> TYPE: DNA
<213> ORGANISM: Artificial Sequence
<220> FEATURE:
<223> OTHER INFORMATION: HV 1-R10

<400> SEQUENCE: 44
caagcagaag acggcatacg agatttcgcg gagtgactgg agttcagacg tgtgctcttc    60
cgatctgagg atggtggtca aggg                                          84

<210> SEQ ID NO 45
<211> LENGTH: 84
<212> TYPE: DNA
<213> ORGANISM: Artificial Sequence
<220> FEATURE:
<223> OTHER INFORMATION: HV 1-R11

<400> SEQUENCE: 45
caagcagaag acggcatacg agatgcgcga gagtgactgg agttcagacg tgtgctcttc    60
cgatctgagg atggtggtca aggg                                          84

<210> SEQ ID NO 46
<211> LENGTH: 84
<212> TYPE: DNA
<213> ORGANISM: Artificial Sequence
<220> FEATURE:
<223> OTHER INFORMATION: HV 1-R12

<400> SEQUENCE: 46
caagcagaag acggcatacg agatctatcg ctgtgactgg agttcagacg tgtgctcttc    60
cgatctgagg atggtggtca aggg                                          84

<210> SEQ ID NO 47
<211> LENGTH: 90
<212> TYPE: DNA
<213> ORGANISM: Artificial Sequence
<220> FEATURE:
<223> OTHER INFORMATION: HV 2-F1

<400> SEQUENCE: 47
aatgatacgg cgaccaccga gatctacacc ctatcctaca ctctttccct acacgacgct    60
cttccgatct caccctatta accactcacg                                    90

<210> SEQ ID NO 48
<211> LENGTH: 90
<212> TYPE: DNA
<213> ORGANISM: Artificial Sequence
<220> FEATURE:
<223> OTHER INFORMATION: HV 2-F2

<400> SEQUENCE: 48
aatgatacgg cgaccaccga gatctacacg gctctgaaca ctctttccct acacgacgct    60
cttccgatct caccctatta accactcacg                                    90

<210> SEQ ID NO 49
<211> LENGTH: 90
<212> TYPE: DNA
<213> ORGANISM: Artificial Sequence
<220> FEATURE:
<223> OTHER INFORMATION: HV 2-F3

<400> SEQUENCE: 49
aatgatacgg cgaccaccga gatctacact atagcctaca ctctttccct acacgacgct        60
cttccgatct caccctatta accactcacg                                        90

<210> SEQ ID NO 50
<211> LENGTH: 90
<212> TYPE: DNA
<213> ORGANISM: Artificial Sequence
<220> FEATURE:
<223> OTHER INFORMATION: HV 2-F4

<400> SEQUENCE: 50
aatgatacgg cgaccaccga gatctacaca tagaggcaca ctctttccct acacgacgct        60
cttccgatct caccctatta accactcacg                                        90

<210> SEQ ID NO 51
<211> LENGTH: 90
<212> TYPE: DNA
<213> ORGANISM: Artificial Sequence
<220> FEATURE:
<223> OTHER INFORMATION: HV 2-F5

<400> SEQUENCE: 51
aatgatacgg cgaccaccga gatctacaca ggcgaagaca ctctttccct acacgacgct        60
cttccgatct caccctatta accactcacg                                        90

<210> SEQ ID NO 52
<211> LENGTH: 90
<212> TYPE: DNA
<213> ORGANISM: Artificial Sequence
<220> FEATURE:
<223> OTHER INFORMATION: HV 2-F6

<400> SEQUENCE: 52
aatgatacgg cgaccaccga gatctacact aatcttaaca ctctttccct acacgacgct        60
cttccgatct caccctatta accactcacg                                        90

<210> SEQ ID NO 53
<211> LENGTH: 90
<212> TYPE: DNA
<213> ORGANISM: Artificial Sequence
<220> FEATURE:
<223> OTHER INFORMATION: HV 2-F7

<400> SEQUENCE: 53
aatgatacgg cgaccaccga gatctacacc aggacgtaca ctctttccct acacgacgct        60
cttccgatct caccctatta accactcacg                                        90

<210> SEQ ID NO 54
<211> LENGTH: 90
<212> TYPE: DNA
<213> ORGANISM: Artificial Sequence
<220> FEATURE:
<223> OTHER INFORMATION: HV 2-F8

<400> SEQUENCE: 54
aatgatacgg cgaccaccga gatctacacg tactgacaca ctctttccct acacgacgct        60
cttccgatct caccctatta accactcacg                                        90

<210> SEQ ID NO 55
<211> LENGTH: 86
<212> TYPE: DNA
<213> ORGANISM: Artificial Sequence

```
<220> FEATURE:
<223> OTHER INFORMATION: HV 2-R1

<400> SEQUENCE: 55
caagcagaag acggcatacg agatcgagta atgtgactgg agttcagacg tgtgctcttc     60
cgatctctgg ttaggctggt gttagg                                         86

<210> SEQ ID NO 56
<211> LENGTH: 86
<212> TYPE: DNA
<213> ORGANISM: Artificial Sequence
<220> FEATURE:
<223> OTHER INFORMATION: HV 2-R2

<400> SEQUENCE: 56
caagcagaag acggcatacg agattctccg gagtgactgg agttcagacg tgtgctcttc     60
cgatctctgg ttaggctggt gttagg                                         86

<210> SEQ ID NO 57
<211> LENGTH: 86
<212> TYPE: DNA
<213> ORGANISM: Artificial Sequence
<220> FEATURE:
<223> OTHER INFORMATION: HV 2-R3

<400> SEQUENCE: 57
caagcagaag acggcatacg agataatgag cggtgactgg agttcagacg tgtgctcttc     60
cgatctctgg ttaggctggt gttagg                                         86

<210> SEQ ID NO 58
<211> LENGTH: 86
<212> TYPE: DNA
<213> ORGANISM: Artificial Sequence
<220> FEATURE:
<223> OTHER INFORMATION: HV 2-R4

<400> SEQUENCE: 58
caagcagaag acggcatacg agatggaatc tcgtgactgg agttcagacg tgtgctcttc     60
cgatctctgg ttaggctggt gttagg                                         86

<210> SEQ ID NO 59
<211> LENGTH: 86
<212> TYPE: DNA
<213> ORGANISM: Artificial Sequence
<220> FEATURE:
<223> OTHER INFORMATION: HV 2-R5

<400> SEQUENCE: 59
caagcagaag acggcatacg agatttctga atgtgactgg agttcagacg tgtgctcttc     60
cgatctctgg ttaggctggt gttagg                                         86

<210> SEQ ID NO 60
<211> LENGTH: 86
<212> TYPE: DNA
<213> ORGANISM: Artificial Sequence
<220> FEATURE:
<223> OTHER INFORMATION: HV 2-R6

<400> SEQUENCE: 60
caagcagaag acggcatacg agatacgaat tcgtgactgg agttcagacg tgtgctcttc     60
cgatctctgg ttaggctggt gttagg                                         86
```

<210> SEQ ID NO 61
<211> LENGTH: 86
<212> TYPE: DNA
<213> ORGANISM: Artificial Sequence
<220> FEATURE:
<223> OTHER INFORMATION: HV 2-R7

<400> SEQUENCE: 61
caagcagaag acggcatacg agatagcttc aggtgactgg agttcagacg tgtgctcttc    60
cgatctctgg ttaggctggt gttagg                                         86

<210> SEQ ID NO 62
<211> LENGTH: 86
<212> TYPE: DNA
<213> ORGANISM: Artificial Sequence
<220> FEATURE:
<223> OTHER INFORMATION: HV 2-R8

<400> SEQUENCE: 62
caagcagaag acggcatacg agatgcgcat tagtgactgg agttcagacg tgtgctcttc    60
cgatctctgg ttaggctggt gttagg                                         86

<210> SEQ ID NO 63
<211> LENGTH: 86
<212> TYPE: DNA
<213> ORGANISM: Artificial Sequence
<220> FEATURE:
<223> OTHER INFORMATION: HV 2-R9

<400> SEQUENCE: 63
caagcagaag acggcatacg agatcatagc cggtgactgg agttcagacg tgtgctcttc    60
cgatctctgg ttaggctggt gttagg                                         86

<210> SEQ ID NO 64
<211> LENGTH: 86
<212> TYPE: DNA
<213> ORGANISM: Artificial Sequence
<220> FEATURE:
<223> OTHER INFORMATION: HV 2-R10

<400> SEQUENCE: 64
caagcagaag acggcatacg agatttcgcg gagtgactgg agttcagacg tgtgctcttc    60
cgatctctgg ttaggctggt gttagg                                         86

<210> SEQ ID NO 65
<211> LENGTH: 86
<212> TYPE: DNA
<213> ORGANISM: Artificial Sequence
<220> FEATURE:
<223> OTHER INFORMATION: HV 2-R11

<400> SEQUENCE: 65
caagcagaag acggcatacg agatgcgcga gagtgactgg agttcagacg tgtgctcttc    60
cgatctctgg ttaggctggt gttagg                                         86

<210> SEQ ID NO 66
<211> LENGTH: 86
<212> TYPE: DNA
<213> ORGANISM: Artificial Sequence
<220> FEATURE:
<223> OTHER INFORMATION: HV 2-R12

<400> SEQUENCE: 66

```
caagcagaag acggcatacg agatctatcg ctgtgactgg agttcagacg tgtgctcttc        60
cgatctctgg ttaggctggt gttagg                                             86

<210> SEQ ID NO 67
<211> LENGTH: 20
<212> TYPE: DNA
<213> ORGANISM: Artificial Sequence
<220> FEATURE:
<223> OTHER INFORMATION: HV 2-1

<400> SEQUENCE: 67
caccctatta accactcacg                                                    20

<210> SEQ ID NO 68
<211> LENGTH: 20
<212> TYPE: DNA
<213> ORGANISM: Artificial Sequence
<220> FEATURE:
<223> OTHER INFORMATION: HV 2-2

<400> SEQUENCE: 68
ctggttaggc tggtgttagg                                                    20
```

PRIMER SET FOR PREPARATION OF NGS LIBRARY AND METHOD AND KIT FOR MAKING NGS LIBRARY USING THE SAME

CROSS-REFERENCE TO RELATED APPLICATIONS

This application claims priority under 35 U.S.C. § 119 of Korean Patent Application No. 10-2015-0150278 filed Oct. 28, 2015. The disclosure of such Korean priority patent application is hereby incorporated herein by reference in its entirety, for all purposes.

TECHNICAL FIELD

The present disclosure relates to a primer set for preparation of a library used for next generation sequencing (NGS), and a method and a kit for making an NGS library using the same, and more specifically, to a primer set prepared to be usable for the NGS by effectively amplifying target DNA in various samples, and a method and a kit for making an NGS library using the same.

BACKGROUND ART

A next generation sequencing technology is able to produce large amounts of data in a short time to remarkably reduce time and cost required for genome decoding as compared to the existing method. In the next generation sequencing technology, sequencing platforms have been developed, and analyzing cost is gradually cheaper over time, and it has succeeded in finding genes responsible for diseases by using the next generation sequencing technology in Mendelian genetic disorder, rare diseases, cancer, etc. According to the most frequently used next generation sequencing of Illumina Inc., DNA is extracted from a sample, and is subjected to mechanical fragmentation, to prepare a library having a specific size, and the library is used for sequencing. Next, initial sequencing data are produced by repeating four kinds of complementary nucleotide binding and isolation reactions with one base unit by using a large sequencing equipment, followed by analysis steps using bioinformatics such as trimming of initial data, mapping, identification of genome mutation, analysis of mutation information (annotation), etc.

The next generation sequencing technology has contributed to creation of new added value through development of innovative drug and industrialization by discovering genome mutations that may have an effect on or may have a possibility of affecting diseases and various biological forms (phenotypes). The next generation sequencing technology is applicable to decoding of DNA as well as RNA and methylation, which makes it possible to perform whole exome sequencing (WES) in which only an exome region encoding protein is captured for sequencing.

Meanwhile, library preparation in the NGS is a process of preparing a library required for sequence analysis by bonding an adapter in the 5' to 3' direction in random DNA or cDNA fragment of the sample. The NGS library preparation in the initial stage required complicated processes such as random cleavage of DNA or RNA sample, 3' and 5' end repair, adapter ligation, PCR amplification, purification, etc., and a long period of time of 1 day to 2 days. The Illumina, Inc., developed a tagmentation method such as "Nextera XT DNA library Preparation" by improving the initial stage of NGS library preparation. The tagmentation method is a method of treating a composite in which a tag (the existing adapter) is bound to a transposome, in sample DNA, followed by cleavage and adapter ligation at the same time, and amplification by PCR, which reduces time required for preparing the library in 8 samples to 3 hours.

However, when analyzing large amounts of samples, the tagmentation method also requires labor and experimental time of an experimenter since it has a number of steps as follows. The tagmentation method is disadvantageous in that the sequencing is able to be performed after quantifying each DNA of the large amounts of samples to perform tagmentation, confirming a size of a product obtained after the tagmentation, followed by purification, amplification by PCR, purification of an amplified PCR product, and library normalization in the same amount.

Accordingly, the present inventors made an effort to develop a manner in which only desired information is able to be more simply and effectively obtained from a number of samples by reversely considering the concept of NGS obtaining a lot of information from a small number of samples while solving the above-described problems, and as a result, confirmed that when a primer set including all of an adapter sequence, an index sequence, and a target DNA specific-sequence was used, library preparation could be completed by performing PCR once, and completed the present disclosure.

DISCLOSURE

Technical Problem

An object of the present disclosure is to provide a primer set for preparation of a next generation sequencing (NGS) library capable of analyzing sequences of target DNA in various samples.

Another object of the present disclosure is to provide a method for making a next generation sequencing (NGS) library capable of analyzing sequences of target DNA in various samples, using a combination of the primer sets.

Still another object of the present disclosure is to provide a kit for making a next generation sequencing (NGS) library including the combination of the primer sets.

Technical Solution

In order to achieve the foregoing objects, the present disclosure provides a primer set for preparation of a next generation sequencing (NGS) library including: a first primer consisting of a first adapter sequence, a first index sequence, a first sequencing sequence, and a first target sequence, and a second primer consisting of a second adapter sequence, a second index sequence, a second sequencing sequence, and a second target sequence.

In addition, the present disclosure provides a method for making a next generation sequencing (NGS) library including: (a) amplifying target DNA using a combination of the primer sets as described above; and (b) library pooling by purifying the amplified product.

Still another object of the present disclosure is to provide a kit for making a next generation sequencing (NGS) library including the combination of the primer sets as described above.

DESCRIPTION OF DRAWINGS

FIG. 3 shows combinations of the primer sets for next generation sequencing (NGS) used in the present disclosure.

FIG. 4 shows comparison between NGS analysis results obtained by an exemplary embodiment of the present disclosure and results obtained by the existing Sanger sequencing method.

BEST MODE

Figure 1:
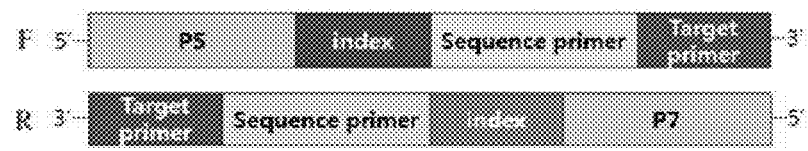
FIG. 1 is a conceptual diagram of a primer set according to the present disclosure.
Figure 2:
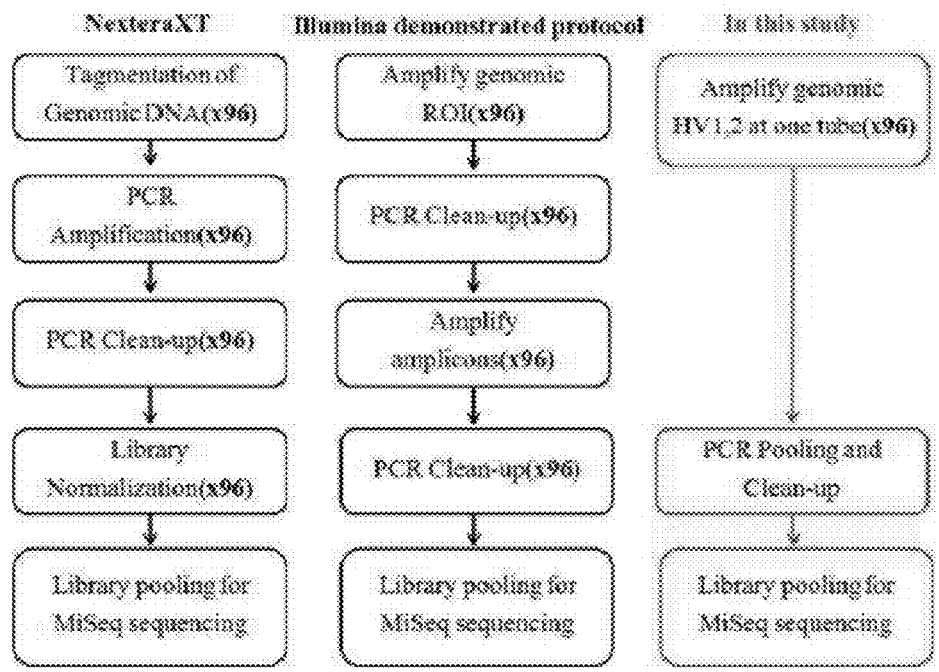
FIG. 2 is a conceptual diagram showing comparison between a method for making a library using the primer set according to the present disclosure and other methods.

As far as it is not defined in other ways, all technical and scientific terms used in the present specification have the same meaning as being generally appreciated by those skilled in the art to which the present disclosure pertains. In general, a nomenclature used in the present specification is well known in technical fields and generally used.

In the present disclosure, it was attempted to confirm that when a next generation sequencing (NGS) library is prepared by combining a target DNA-specific primer and a primer for preparing an NGS library, it is possible to amplify target DNA desirable for being analyzed in large amounts of samples and to analyze the target DNA through sequence analysis using the NGS.

In the present disclosure, an integrated primer including all of a primer specifically bound to the target DNA, and an adapter primer, an index primer, and a sequencing primer essential for preparing the NGS library was prepared to be used for preparation of the library for NGS. As a result, it was confirmed that it was possible to prepare the library for NGS through a single PCR and purification process.

Specifically, according to an exemplary embodiment of the present disclosure, it could be confirmed that when the library for NGS was prepared by using an integrated primer including all of a primer specifically bound to a hypervariable region 1 (HV1) of human mitochondrial DNA, and a P5 or P7 adapter primer, an index primer, and a sequencing primer, it was possible to more simply and rapidly prepare the library for NGS as compared to the existing methods.

Therefore, according to an aspect of the present disclosure, the present disclosure relates to a primer set for preparation of a next generation sequencing (NGS) library including: a first primer consisting of a first adapter sequence, a first index sequence, a first sequencing sequence, and a first target sequence, and a second primer consisting of a second adapter sequence, a second index sequence, a second sequencing sequence, and a second target sequence.

In the present disclosure, the first adapter sequence may be P5 (SEQ ID NO: 1), and the second adapter sequence may be P7 (SEQ ID NO: 2).

```
                                              (SEQ ID NO: 1)
P5      5'-AATGATACGGCGACCACCGAGATCTACAC-3'

(SEQ ID NO: 2)
P7      5'-CAAGCAGAAGACGGCATACGAGAT-3'
```

In the present disclosure, the first index sequence may be any one sequence selected from the group consisting of SEQ ID NO: 3 to SEQ ID NO: 10, and the second index sequence may be any one sequence selected from the group consisting of SEQ ID NO: 11 to SEQ ID NO: 22.

TABLE 1

The information of index sequence
index sequence

| SEQ ID NO | first index | sequence | SEQ ID NO | Second index | sequence |
|---|---|---|---|---|---|
| 3 | D501 | TATAGCCT | 11 | D701 | CGAGTAAT |
| 4 | D502 | ATAGAGGC | 12 | D702 | TCTCCGGA |
| 5 | D503 | CCTATCCT | 13 | D703 | AATGAGCG |
| 6 | D504 | GGCTCTGA | 14 | D704 | GGAATCTC |
| 7 | D505 | AGGCGAAG | 15 | D705 | TTCTGAAT |
| 8 | D506 | TAATCTTA | 16 | D706 | ACGAATTC |
| 9 | D507 | CAGGACGT | 17 | D707 | AGCTTCAG |
| 10 | D508 | GTACTGAC | 18 | D708 | GCGCATTA |
| | | | 19 | D709 | CATAGCCG |
| | | | 20 | D7010 | TTCGCGGA |
| | | | 21 | D7011 | GCGCGAGA |
| | | | 22 | D7012 | CTATCGCT |

The sequencing sequence of the present disclosure is available without limitation as long as it is commonly applied for sequence analysis in NGS equipment. Preferably, the sequencing sequence of the first primer or the third primer may be SEQ ID NO: 23, and the sequencing sequence of the second primer or the fourth primer may be SEQ ID NO: 24.

```
                                             (SEQ ID NO: 23)
5'-ACACTCTTTCCCTACACGACGCTCTTCCGATCT-3'

(SEQ ID NO: 24)
5'-GTGACTGGAGTTCAGACGTGTGCTCTTCCGATCT-3'
```

In the present disclosure, the first target sequence and the second target sequence are available without limitation as long as they are able to be specifically bound to the target DNA. Preferably, the first target sequence and the second target sequence are bound to a specific region of the target DNA, and more preferably, they are bound to the hypervariable region 1 (HV1) of human mitochondrial DNA, and the most preferably, the first target sequence and the second target sequence are SEQ ID NO: 25 and SEQ ID NO: 26.

```
5'-CTCCACCATTAGCACCCAAA-3'      (SEQ ID NO: 25)

5'-GAGGATGGTGGTCAAGGG-3'        (SEQ ID NO: 26)
```

In the present disclosure, the first primer may be any one of SEQ ID NO: 27 to SEQ ID NO: 34, and the second primer may be any one of SEQ ID NO: 35 to SEQ ID NO: 46.

TABLE 2

The primer of present application

| SEQ ID NO | primer | sequence |
|---|---|---|
| 27 | HV1-F1 | 5'-AATGATACGGCGACCACCGAGATCTACACCCTATCCTACACTCTTTCCCTACACGACGCTCTTCCGATCTCTCCACCATTAGCACCCAAA-3' |
| 28 | HV1-F2 | 5'-AATGATACGGCGACCACCGAGATCTACACGGCTCTGAACACTCTTTCCCTACACGACGCTCTTCCGATCTCTCCACCATTAGCACCCAAA-3' |
| 29 | HV1-F3 | 5'-AATGATACGGCGACCACCGAGATCTACACTATAGCCTACACTCTTTCCCTACACGACGCTCTTCCGATCTCTCCACCATTAGCACCCAAA-3' |
| 30 | HV1-F4 | 5'-AATGATACGGCGACCACCGAGATCTACACATAGAGGCACACTCTTTCCCTACACGACGCTCTTCCGATCTCTCCACCATTAGCACCCAAA-3' |
| 31 | HV1-F5 | 5'-AATGATACGGCGACCACCGAGATCTACACAGGCGAAGACACTCTTTCCCTACACGACGCTCTTCCGATCTCTCCACCATTAGCACCCAAA-3' |
| 32 | HV1-F6 | 5'-AATGATACGGCGACCACCGAGATCTACACTAATCTTAACACTCTTTCCCTACACGACGCTCTTCCGATCTCTCCACCATTAGCACCCAAA-3' |
| 33 | HV1-F7 | 5'-AATGATACGGCGACCACCGAGATCTACACCAGGACGTACACTCTTTCCCTACACGACGCTCTTCCGATCTCTCCACCATTAGCACCCAAA-3' |
| 34 | HV1-F8 | 5'-AATGATACGGCGACCACCGAGATCTACACGTACTGACACACTCTTTCCCTACACGACGCTCTTCCGATCTCTCCACCATTAGCACCCAAA-3' |
| 35 | HV1-R1 | 5'-CAAGCAGAAGACGGCATACGAGATCGAGTAATGTGACTGGAGTTCAGACGTGTGCTCTTCCGATCTGAGGATGGTGGTCAAGGG-3' |
| 36 | HV1-R2 | 5'-CAAGCAGAAGACGGCATACGAGATTCTCCGGAGTGACTGGAGTTCAGACGTGTGCTCTTCCGATCTGAGGATGGTGGTCAAGGG-3' |
| 37 | HV1-R3 | 5'-CAAGCAGAAGACGGCATACGAGATAATGAGCGGTGACTGGAGTTCAGACGTGTGCTCTTCCGATCTGAGGATGGTGGTCAAGGG-3' |
| 38 | HV1-R4 | 5'-CAAGCAGAAGACGGCATACGAGATGGAATCTCGTGACTGGAGTTCAGACGTGTGCTCTTCCGATCTGAGGATGGTGGTCAAGGG-3' |
| 39 | HV1-R5 | 5'-CAAGCAGAAGACGGCATACGAGATTTCTGAATGTGACTGGAGTTCAGACGTGTGCTCTTCCGATCTGAGGATGGTGGTCAAGGG-3' |
| 40 | HV1-R6 | 5'-CAAGCAGAAGACGGCATACGAGATACGAATTCGTGACTGGAGTTCAGACGTGTGCTCTTCCGATCTGAGGATGGTGGTCAAGGG-3' |
| 41 | HV1-R7 | 5'-CAAGCAGAAGACGGCATACGAGATAGCTTCAGGTGACTGGAGTTCAGACGTGTGCTCTTCCGATCTGAGGATGGTGGTCAAGGG-3' |
| 42 | HV1-R8 | 5'-CAAGCAGAAGACGGCATACGAGATGCGCATTAGTGACTGGAGTTCAGACGTGTGCTCTTCCGATCTGAGGATGGTGGTCAAGGG-3' |
| 43 | HV1-R9 | 5'-CAAGCAGAAGACGGCATACGAGATCATAGCCGGTGACTGGAGTTCAGACGTGTGCTCTTCCGATCTGAGGATGGTGGTCAAGGG-3' |
| 44 | HV1-R10 | 5'-CAAGCAGAAGACGGCATACGAGATTTCGCGGAGTGACTGGAGTTCAGACGTGTGCTCTTCCGATCTGAGGATGGTGGTCAAGGG-3' |

TABLE 2-continued

The primer of present application

| SEQ ID NO | primer | sequence |
|---|---|---|
| 45 | HV1-R11 | 5'-CAAGCAGAAGACGGCATACGAGATGCGCGAGAGTGACTGGAGTTCAGACGTGTGCTCTTCCGATCTGAGGATGGTGGTCAAGGG-3' |
| 46 | HV1-R12 | 5'-CAAGCAGAAGACGGCATACGAGATCTATCGCTGTGACTGGAGTTCAGACGTGTGCTCTTCCGATCTGAGGATGGTGGTCAAGGG-3' |
| 47 | HV2-F1 | 5'-AATGATACGGCGACCACCGAGATCTACACCCTATCCTACACTCTTTCCCTACACGACGCTCTTCCGATCTCACCCTATTAACCACTCACG-3' |
| 48 | HV2-F2 | 5'-AATGATACGGCGACCACCGAGATCTACACGGCTCTGAACACTCTTTCCCTACACGACGCTCTTCCGATCTCACCCTATTAACCACTCACG-3' |
| 49 | HV2-F3 | 5'-AATGATACGGCGACCACCGAGATCTACACTATAGCCTACACTCTTTCCCTACACGACGCTCTTCCGATCTCACCCTATTAACCACTCACG-3' |
| 50 | HV2-F4 | 5'-AATGATACGGCGACCACCGAGATCTACACATAGAGGCACACTCTTTCCCTACACGACGCTCTTCCGATCTCACCCTATTAACCACTCACG-3' |
| 51 | HV2-F5 | 5'-AATGATACGGCGACCACCGAGATCTACACAGGCGAAGACACTCTTTCCCTACACGACGCTCTTCCGATCTCACCCTATTAACCACTCACG-3' |
| 52 | HV2-F6 | 5'-AATGATACGGCGACCACCGAGATCTACACTAATCTTAACACTCTTTCCCTACACGACGCTCTTCCGATCTCACCCTATTAACCACTCACG-3' |
| 53 | HV2-F7 | 5'-AATGATACGGCGACCACCGAGATCTACACCAGGACGTACACTCTTTCCCTACACGACGCTCTTCCGATCTCACCCTATTAACCACTCACG-3' |
| 54 | HV2-F8 | 5'-AATGATACGGCGACCACCGAGATCTACACGTACTGACACACTCTTTCCCTACACGACGCTCTTCCGATCTCACCCTATTAACCACTCACG-3' |
| 55 | HV2-R1 | 5'-CAAGCAGAAGACGGCATACGAGATCGAGTAATGTGACTGGAGTTCAGACGTGTGCTCTTCCGATCTCTGGTTAGGCTGGTGTTAGG-3' |
| 56 | HV2-R2 | 5'-CAAGCAGAAGACGGCATACGAGATTCTCCGGAGTGACTGGAGTTCAGACGTGTGCTCTTCCGATCTCTGGTTAGGCTGGTGTTAGG-3' |
| 57 | HV2-R3 | 5'-CAAGCAGAAGACGGCATACGAGATAATGAGCGGTGACTGGAGTTCAGACGTGTGCTCTTCCGATCTCTGGTTAGGCTGGTGTTAGG-3' |
| 58 | HV2-R4 | 5'-CAAGCAGAAGACGGCATACGAGATGGAATCTCGTGACTGGAGTTCAGACGTGTGCTCTTCCGATCTCTGGTTAGGCTGGTGTTAGG-3' |
| 59 | HV2-R5 | 5'-CAAGCAGAAGACGGCATACGAGATTTCTGAATGTGACTGGAGTTCAGACGTGTGCTCTTCCGATCTCTGGTTAGGCTGGTGTTAGG-3' |
| 60 | HV2-R6 | 5'-CAAGCAGAAGACGGCATACGAGATACGAATTCGTGACTGGAGTTCAGACGTGTGCTCTTCCGATCTCTGGTTAGGCTGGTGTTAGG-3' |
| 61 | HV2-R7 | 5'-CAAGCAGAAGACGGCATACGAGATAGCTTCAGGTGACTGGAGTTCAGACGTGTGCTCTTCCGATCTCTGGTTAGGCTGGTGTTAGG-3' |
| 62 | HV2-R8 | 5'-CAAGCAGAAGACGGCATACGAGATGCGCATTAGTGACTGGAGTTCAGACGTGTGCTCTTCCGATCTCTGGTTAGGCTGGTGTTAGG-3' |

TABLE 2-continued

The primer of present application

| SEQ ID NO | primer | sequence |
|---|---|---|
| 63 | HV2-R9 | 5'-CAAGCAGAAGACGGCATACGAGATCATAGCCGGTGACTGGAGTTCAGACGTGTGCTCTTCCGATCTCTGGTTAGGCTGGTGTTAGG-3' |
| 64 | HV2-R10 | 5'-CAAGCAGAAGACGGCATACGAGATTTCGCGGAGTGACTGGAGTTCAGACGTGTGCTCTTCCGATCTCTGGTTAGGCTGGTGTTAGG-3' |
| 65 | HV2-R11 | 5'-CAAGCAGAAGACGGCATACGAGATGCGCGAGAGTGACTGGAGTTCAGACGTGTGCTCTTCCGATCTCTGGTTAGGCTGGTGTTAGG-3' |
| 66 | HV2-R12 | 5'-CAAGCAGAAGACGGCATACGAGATCTATCGCTGTGACTGGAGTTCAGACGTGTGCTCTTCCGATCTCTGGTTAGGCTGGTGTTAGG-3' |

The target DNA of the present disclosure is DNA isolated from tissue selected from the group consisting of blood, semen, vaginal cells, hair, saliva, urine, buccal cells, amniotic fluids containing placental cells or fetal cells, and a mixture thereof, but is not limited thereto.

The target DNA of the present disclosure may be obtained by a general method known in the art. For example, the DNA may be isolated by treating the tissue with a DNA lysis buffer (e.g., tris-HCl, EDTA, EGTA, SDS, deoxycholate, and tritonX, and/or NP-40), but the method for obtaining the DNA is not limited thereto.

Meanwhile, it was predicted that when there are several target DNAs, the primers may be variously combined to prepare the library.

According to another exemplary embodiment of the present disclosure, it could be confirmed that when the library for NGS was prepared by using an integrated primer including all of a primer specifically bound to a hypervariable region 1 (HV1) or to a hypervariable region 2 (HV2) of human mitochondrial DNA, and a P5 or P7 adapter primer, an index primer, and a sequencing primer, it was possible to rapidly prepare the library for NGS.

Therefore, according to another aspect of the present disclosure, the present disclosure relates to a combination of primer sets: including the primer set as described above, and further including a primer set including a third primer consisting of a first adapter sequence, a first index sequence, a first sequencing sequence, and a third target sequence, and a fourth primer consisting of a second adapter sequence, a second index sequence, a second sequencing sequence, and a fourth target sequence.

In the present disclosure, the third target sequence may be the hypervariable region 2 (HV2) of the human mitochondrial DNA.

In the present disclosure, the third target sequence and the fourth target sequence are available without limitation as long as they are able to be specifically bound to the target DNA. Preferably, the third target sequence and the fourth target sequence are bound to a specific region of the target DNA, and more preferably, they are bound to the hypervariable region 2 (HV2) of the human mitochondrial DNA, and the most preferably, the third target sequence and the fourth target sequence are SEQ ID NO: 67 and SEQ ID NO: 68.

5'-CACCCTATTAACCACTCACG-3'     (SEQ ID NO: 67)

5'-CTGGTTAGGCTGGTGTTAGG-3'     (SEQ ID NO: 68)

In the present disclosure, the third primer may be any one of SEQ ID NO: 47 to SEQ ID NO: 54, and the fourth primer may be any one of SEQ ID NO: 55 to SEQ ID NO: 66.

In the present disclosure, the combination of primer sets may include the primer set and further include 1 to 22 primer set(s) of which only the target sequence is different from that of the primer set. Specifically, the combination of primer sets of the present disclosure may simultaneously detect 1 to 48 target(s).

In addition, the present disclosure relates to a method for making a next generation sequencing (NGS) library including: (a) extracting DNA from a sample; (b) amplifying target DNA using the combination of primer sets as described above; and (c) library pooling by purifying the amplified product.

In the present disclosure, the DNA is available as long as it is a nucleic acid containing the target DNA, but preferably, may be mitochondrial DNA.

In the present disclosure, the target DNA may be HV1 or HV2 of mitochondria.

The target DNA of the present disclosure is a biological sample including DNA. Meanwhile, the target DNA may be a single-source sample or a mixed sample of two or more sources.

The method of the present disclosure may be applied to DNA isolated from the biological sample, but direct polymerase chain reaction in which a nucleic acid molecule is involved may be performed by directly using the biological sample (see Korean Patent Registration No. 10-0746372).

The term "amplification" in this disclosure means a reaction for amplifying nucleic acid molecules. Various amplification reactions are known in the art, and include a polymerase chain reaction (hereinafter, referred to as PCR) (U.S. Pat. Nos. 4,683,195, 4,683,202, and 4,800,159), reverse transcription-polymerase chain reaction (hereinafter, referred to as RT-PCR) (Sambrook et al., Molecular Cloning. A Laboratory Manual, 3rd ed. Cold Spring Harbor Press (2001)), methods of Miller, H. I. (WO 89/06700) and Davey, C., et al., (EP 329,822), ligase chain reaction (LCR)(17, 18), Gap-LCR (WO 90/01069), repair chain reaction (EP 439, 182), transcription-mediated amplification (TMA)(19) (WO 88/10315), self sustained sequence replication (20)(WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245), nucleic acid sequence based amplification (NASBA) (U.S. Pat. Nos. 5,130,238, 5,409,818, 5,554,517, and 6,063,603), strand displacement amplification, and loop-mediated isothermal amplification (LAMP), but the amplification reactions are not limited thereto.

Other amplification methods to be usable are described in U.S. Pat. Nos. 5,242,794, 5,494,810, 4,988,617, and 6,582,938.

PCR is the most well-known nucleic acid amplification method, and a number of modifications and applications of PCR have been developed. For example, in order to enhance specificity or sensitivity of the PCR, touchdown PCR, hot start PCR, nested PCR, and booster PCR were developed by modifying traditional PCR procedures. In addition, multiplex PCR, real-time PCR, differential display PCR (D-PCR), rapid amplification of cDNA ends (RACE), inverse polymerase chain reaction (IPCR), vectorette PCR, and thermal asymmetric interlaced PCR (TAIL-PCR) were developed for specific application.

The PCR is described in more detail in document [McPherson, M. J., and Moller, S. G. PCR. BIOS Scientific Publishers, Springer-Verlag New York Berlin Heidelberg, N.Y. (2000)], the entire disclosure of which is incorporated herein by reference.

In the present disclosure, the method for purifying the amplified product is available as long as it is any purification method generally known in the art. Preferably, the purification method may be selected from the group consisting of gel filtration, a method using a column, and a method using an electromagnetic field.

Further, the present disclosure relates to a kit for making a next generation sequencing (NGS) library including the combination of primer sets as described above.

The kit of the present disclosure includes a first container containing a DNA cleaving agent, and at least one container containing an integrated primer combination for amplifying the target DNA. The combination of primer sets used according to the present disclosure includes sequences of SEQ ID NO: 27 to SEQ ID NO: 66, a functional combination, and a fragment thereof.

In the present disclosure, the kit may selectively include a buffer, a DNA polymerase cofactor, and a reagent required for performing a target amplification PCR reaction (for example, PCR reaction) such as deoxyribonucleotide-5-triphosphate, and may include various polynucleotide molecules, reverse transcriptase, various buffers and reagents, and antibodies inhibiting DNA polymerase activity.

When the kit of the present disclosure is used, it is possible to make the library for NGS by performing simultaneous multiplex PCR that simultaneously uses two or more kinds of primer sets prepared in the present disclosure with the common PCR condition, wherein the PCR is performed once.

EXAMPLE

Hereinafter, the present disclosure will be described in detail with reference to the following Examples. However, the following Examples are only for exemplifying the present disclosure, and it will be obvious to those skilled in the art that the scope of the present disclosure is not construed to be limited to these examples.

Example 1: Preparation of Integrated Primer for NGS Library for Amplification of Specific Regions in Large Amounts of Samples 1.1 Preparation of Samples Oral cells were collected from a total of 91 Koreans without blood relationship, and DNAs thereof were extracted by using a QIAGEN Microkit (QIAGEN, Hilden, Germany) The extracted DNAs were stored at 4° C.

1.2 Primer Design and PCR

An integrated primer set including an adapter (P7 or P5 region, index, sequencing primer) designed by applying NGS manner with regard to the hypervariable region 1 (hereinafter, referred to as HV1) and the hypervariable region 2 (hereinafter, referred to as HV2) of the mitochondrial DNA, and the existing known primers of HV1 and HV2, in the 5' to 3' direction, was prepared (FIG. 1).

The HV1 and HV2 integrated primer set had different indexes provided by Illumina, Inc., such that a total of 96 sample analysis could be performed by performing PCR once, and the HV1 and the HV2 for each sample could be amplified at a time. PCR amplification condition was as follows: denaturation at 96° C. for 15 minutes, denaturation at 94° C. for 15 seconds, annealing at 56° C. for 30 seconds, extension at 72° C. for 1 minute 35 times, followed by extension at 72° C. for 7 minutes. 4 µl of the amplified PCR product was mixed with the same amount of 2× loading dye, and the mixed product was subjected to electrophoresis in 2% agarose gel at 110V for 10 minutes, and gel bands were confirmed by using a UV transilluminator. The entire amplified PCR product (HV1 and HV2) was collected and purified by using a QIAquick® PCR Purification kit (QIAGEN, Hilden, Germany) A concentration of the purified PCR product was quantified, and the PCR product was tested in MiSeq equipment according to methods provided by Illumina, Inc.

1.3 NGS Data Analysis

The sequencing results were analyzed by using a MiSeq Reporter (MSR; Illumina, Inc., San Diego, Calif.; v2.5.1) created on the basis of mapping programs, BWA (Burrows-Wheeler Aligner) and GATK (Genome Analysis ToolKit).

As a result, it was confirmed that when comparing results between the method of the present disclosure and the existing Sanger sequencing, 30666 base pairs (bp) out of a total of 30690 base pairs were identical in the HV1, and 17275 base pairs out of a total of 17280 base pairs were identical in the HV2, and thus, it could be appreciated that accuracy was high (FIG. 4).

The method for making the next generation sequencing (NGS) library using the primer set according to the present disclosure is able to simply analyze large amounts of samples as compared to the existing method for making a library, and a tagmentation method (Illumina, Inc.), which is effectively usable for analysis of the target DNA sequences and for database construction, in large amounts of samples.

Although specific embodiments of the present disclosure are described in detail, it will be apparent to those skilled in the art that the specific description is merely desirable exemplary embodiment and should not be construed as limiting the scope of the present disclosure. Therefore, the substantial scope of the present disclosure is defined by the accompanying claims and equivalent thereof.

The invention claimed is:

1. A primer set for preparation of a next generation sequencing (NGS) library comprising: a first primer consisting of a first adapter sequence, a first index sequence, a first sequencing sequence, and a first target sequence, and a second primer consisting of a second adapter sequence, a second index sequence, a second sequencing sequence, and a second target sequence, wherein the first primer is selected from the group consisting of SEQ ID NO: 27 to SEQ ID NO: 34, and the second primer is selected form the group consisting of SEQ ID NO: 35 to SEQ ID NO: 46.

2. The primer set of claim 1, wherein the first adapter sequence is P5 (SEQ ID NO: 1), and the second adapter sequence is P7 (SEQ ID NO: 2).

3. The primer set of claim 1, wherein the first index sequence is selected from the group consisting of SEQ ID NO: 3 to SEQ ID NO: 10, and the second index sequence is selected from the group consisting of SEQ ID NO: 11 to SEQ ID NO: 22.

4. The primer set of claim 1, wherein the first target sequence and the second target sequence are bound to the hypervariable region 1 (HV1) of human mitochondrial DNA.

5. The primer set of claim 1, wherein the first target sequence is SEQ ID NO: 25.

6. The primer set of claim 1, wherein the second target sequence is SEQ ID NO: 26.

7. A combination of primer sets for preparation of a next generation sequencing (NGS) library comprising: the primer set of claim 1; a third primer consisting of a first adapter sequence, a first index sequence, a first sequencing sequence, and a third target sequence; and a fourth primer consisting of a second adapter sequence, a second index sequence, a second sequencing sequence, and a fourth target sequence.

8. The primer combination of claim 7, wherein the third target sequence and the fourth target sequence are bound to the hypervariable region 2 (HV2) of human mitochondrial DNA.

9. The primer combination of claim 7, wherein the third target sequence is SEQ ID NO: 67.

10. The primer combination of claim 7, wherein the fourth target sequence is SEQ ID NO: 68.

11. The primer combination of claim 7, wherein the third primer is selected from the group consisting of SEQ ID NO: 47 to SEQ ID NO: 54, and the fourth primer is selected form the group consisting of SEQ ID NO: 55 to SEQ ID NO: 66.

12. The primer combination of claim 7, wherein the primer sets further comprise 1 to 22 primer set(s) of which only the target sequence is different from that of the primer set of claim 7.

13. A method for making a next generation sequencing (NGS) library comprising:
    (a) extracting DNA from a sample;
    (b) amplifying target DNA using the combination of primer sets of claim 7; and
    (c) library pooling by purifying the amplified product.

14. The method of claim 13, wherein the target DNA is HV1 or HV2 of mitochondria.

15. A kit for making a next generation sequencing (NGS) library comprising the combination of primer sets of claim 7.

* * * * *